United States Patent
Takahashi et al.

(10) Patent No.: US 9,980,694 B2
(45) Date of Patent: May 29, 2018

(54) X-RAY CT APPARATUS AND IMAGE CALCULATING DEVICE FOR X-RAY CT APPARATUS

(71) Applicant: HITACHI, LTD., Tokyo (JP)

(72) Inventors: Hisashi Takahashi, Tokyo (JP); Taiga Goto, Tokyo (JP); Koichi Hirokawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 226 days.

(21) Appl. No.: 15/105,329

(22) PCT Filed: Jan. 23, 2015

(86) PCT No.: PCT/JP2015/051749
§ 371 (c)(1),
(2) Date: Jun. 16, 2016

(87) PCT Pub. No.: WO2015/115309
PCT Pub. Date: Aug. 6, 2015

(65) Prior Publication Data
US 2017/0000442 A1    Jan. 5, 2017

(30) Foreign Application Priority Data

Jan. 28, 2014   (JP) ................. 2014-013695

(51) Int. Cl.
*G01K 1/12* (2006.01)
*A61B 6/00* (2006.01)
(Continued)

(52) U.S. Cl.
CPC ............ *A61B 6/5258* (2013.01); *A61B 6/032* (2013.01); *A61B 6/5205* (2013.01);
(Continued)

(58) Field of Classification Search
None
See application file for complete search history.

(56) References Cited

U.S. PATENT DOCUMENTS

| 5,533,091 A | 7/1996 | Hsieh | |
|---|---|---|---|
| 2003/0156679 A1* | 8/2003 | Mori | A61B 6/00 378/4 |

(Continued)

FOREIGN PATENT DOCUMENTS

| JP | 9-19426 | 1/1997 |
|---|---|---|
| JP | 9-168536 | 6/1997 |

(Continued)

OTHER PUBLICATIONS

International Search Report in PCT/JP2015/051749.

*Primary Examiner* — Hoon Song
(74) *Attorney, Agent, or Firm* — Cooper & Dunham LLP

(57) ABSTRACT

In order to provide a technique capable of restoring measured data from projection data with high accuracy and removing system noise included in the measured data, a signal processing device obtains measured data x including signal values of 0 or less by processing an output signal from a data acquisition system, and performs a conversion process on the measured data x by using a predefined function including a logarithmic function so as to generate projection data (logarithmically converted data z), in which the predefined function is a function of which an inverse function is present for values of a predetermined negative number s or more, and the measured data x including signal values of 0 or less within a predetermined range is restored from the projection data by applying the inverse function to the projection data.

9 Claims, 14 Drawing Sheets

(51) Int. Cl.
    *A61B 6/03*          (2006.01)
    *G01N 23/04*        (2018.01)
    *G06T 11/00*        (2006.01)
    *G06T 7/00*          (2017.01)

(52) U.S. Cl.
    CPC ......... *G01N 23/046* (2013.01); *G06T 7/0012* (2013.01); *G06T 11/005* (2013.01); *G06T 2207/10081* (2013.01)

(56) References Cited

U.S. PATENT DOCUMENTS

| | | | |
|---|---|---|---|
| 2004/0247167 A1 | 12/2004 | Bueno et al. | |
| 2005/0201635 A1 | 9/2005 | Mori | |
| 2011/0268339 A1* | 11/2011 | Volokh | A61B 6/502 |
| | | | 382/132 |
| 2015/0366528 A1* | 12/2015 | Jeong | A61B 6/5258 |
| | | | 378/62 |

FOREIGN PATENT DOCUMENTS

| | | |
|---|---|---|
| JP | 2002-119504 | 4/2002 |
| JP | 2003-310600 | 11/2003 |
| JP | 2004-361407 | 12/2004 |
| JP | 2005-253629 | 9/2005 |

\* cited by examiner

X-RAY CT APPARATUS AND IMAGE CALCULATING DEVICE FOR X-RAY CT APPARATUS

TECHNICAL FIELD

The present invention relates to an X-ray CT apparatus, and particularly to a technique for suppressing image quality deterioration due to system noise during low dose scanning.

BACKGROUND ART

An X-ray CT apparatus applies X-rays from the vicinity of an object, and generates a distribution of X-ray absorption coefficients of the object as an image on the basis of projection data acquired at a plurality of projection angles. As an X-ray irradiation amount is increased, an image with reduced noise can be acquired, and thus image quality is improved. On the other hand, the influence of exposure to X-rays on a human body has been problematic in recent years, and thus a technique has been actively examined in which image quality necessary in a doctor's diagnosis is obtained in low dose scanning in which an X-ray irradiation amount is reduced.

Noise which influences an image obtained by the X-ray CT apparatus is roughly classified into photon noise caused by fluctuation of X-ray photons and system noise which is added in a data collecting system. The former changes according to an X-ray irradiation amount, but the latter exhibits an inherent noise level for each data collecting system. Thus, in a case where an amount of X-rays incident to a detector in low dose scanning is small, a ratio of the system noise occupying an output signal from the data collecting system increases.

PTL 1 discloses a technique in which, when measured data in which a ratio of the noise component is high due to a dose of X-rays incident to a detector being small is converted into projection data, the noise component is prevented from increasing through logarithmic conversion. In other words, in a case where a value of the measured data is equal to or greater than a predetermined value, the measured data is converted into projection data by using a logarithmic function in the same manner as in the related art. However, in a case where a dose of X-rays incident to the detector is small, and a value of the measured data is smaller than the predetermined value, the measured data is converted into projection data by using a function replacing the logarithmic function. Consequently, the noise component is suppressed from increasing and thus appearing as artifacts in an image when the measured data is converted into the projection data.

On the other hand, as techniques of reducing artifacts of an image caused by the photon noise and the system noise included in measured data, a technique of performing bias correction on the measured data or a technique of reconstructing an image through iterative reconstruction based on the measured data is also known.

The bias correction method is a method in which, as disclosed in NPL 1, a value of measured data in a focused element of a detector is corrected through iterative filtering processes while maintaining positivity of the focused element and an average value of the focused element and an adjacent element by referring to a value of measured data in the adjacent element of the focused element. The measured data having undergone the bias correction is converted into projection data by using a logarithmic function, and an image is reconstructed by using the projection data.

In the iterative reconstruction based on the measured data, as disclosed in NPL 2, the iterative reconstruction is performed on the measured data so that an image is reconstructed, without converting the measured data into projection data. Specifically, models of the photon noise and the system noise included in the measured data are generated, and an image is calculated by using an iterative solution on the basis of the models.

CITATION LIST

Patent Literature

PTL 1: Japanese Patent No. 4363834

Non-Patent Literature

NPL 1: J-B. Thibault et. al., "A Recursive Filter for Noise Reduction in Statistical Iterative Tomographic Imaging" Proc. of SPIE 6065, Computational Imaging IV, pp. 60650X, 2006

NPL 2: J. Xu et. al., "Electronic Noise Modeling in-Statistical Iterative Reconstruction," IEEE. Trans. Image. Process., Vol. 18, No. 6, pp. 1228 to 1238, 2009

SUMMARY OF INVENTION

Technical Problem

In the X-ray CT apparatus, in a case where an amount of X-rays incident to the detector is small during low dose scanning, a ratio of the system noise occupying an output signal from the data collecting system increases, and, as a result, a signal may have a value of 0 or less. Thus, in the related art, as disclosed in PTL 1 (paragraph [0020]), offset correction is performed on an output from the detector so that a value smaller than a predetermined positive number (for example, 1) is rounded up to a predetermined positive number, and then logarithmic conversion is performed. However, in a case where the offset correction is performed in which measured data of 0 or less is unconditionally rounded up to a positive number, since characteristics such as strength and weakness of actually measured data disappear, a streak (linear) artifact occurs on an image, or a low frequency CT value increases (a CT value decreases depending on a rounding-up method), and this causes image quality deterioration.

On the other hand, in the method in which measured data is subject to bias correction and is then converted into projection data, and image reconstruction is performed, or the method in which iterative reconstruction based on measured data is performed, a value of the measured data is small, and thus even if values of some signals are equal to or smaller than 0, image quality deterioration in a reconstructed image can be reduced. However, since the bias correction is iterative filtering, and the iterative reconstruction method also uses an iterative solution, both of the methods require a lot of computation time.

In recent years, in the X-ray CT apparatus, a highly accurate image with reduced artifacts has been desirable, and it has also been necessary to generate an image rapidly in order to diagnose an emergency patient. There is a case where a reconstruction condition of previously captured data may be changed, and an image may be reconstructed again.

Therefore, in common to a case where scanning and reconstruction are simultaneously performed and a case where an image is reconstructed again, projection data is created through a typical logarithmic conversion process without performing the iterative image reconstruction method or the bias correction process, and thus a reconstructed image is generated rapidly so as to correspond to examination or the like of an emergency patient. Thereafter, in a case where there is a request from an operator, a highly accurate image from which the system noise is removed may be generated by applying the bias correction or the iterative reconstruction to the same measured data. In this case, if the measured data can be restored from the projection data with which the image is rapidly generated and can be used to generate a highly accurate image, it becomes easier to rapidly generate an image in the case where an image is reconstructed again than in the case where the measured data is preserved.

The projection data obtained through logarithmic conversion of the measured data has a narrower data range than that of the measured data, and thus it is possible to reduce the data storage capacity.

However, since a logarithmic function cannot take a variable which is equal to or less than 0, measured data including a value of 0 or less cannot be restored from projection data with high accuracy.

Since a value of the logarithmic function increases to infinity if a variable is close to 0, measured data cannot be restored with high accuracy from projection data which is preserved in a finite data size. In a case where measured data of 0 or less is rounded up to a positive number through offset correction, and is then subjected to logarithmic conversion, the measured data before the offset correction cannot be restored even if inverse logarithmic conversion is performed, and thus measured data of a small value cannot be accurately restored.

Therefore, in the technique of the related art, it is not possible to restore measured data from projection data and to reduce system noise included in the measured data through an iterative image reconstruction method or a bias correction process.

An object of the invention is to provide a technique in which measured data can be restored from projection data with high accuracy, and system noise included in the measured data can be removed.

Solution to Problem

In order to achieve the object, according to the present invention, there is provided an X-ray CT apparatus including an X-ray generation device that irradiates an object with X-rays; a data acquisition system that detects the X-rays passed through the object; a signal processing device; and a reconstruction calculating device. The signal processing device obtains measured data including signal values of 0 or less by processing an output signal from the data acquisition system, and performs a conversion process on the measured data by using a predefined function including a logarithmic function so as to generate projection data. The reconstruction calculating device performs a reconstruction process on the projection data so as to generate an image. The predefined function is a function of which an inverse function is present for values of a predetermined negative number or more. The measured data including signal values of 0 or less within a predetermined range is restored from the projection data by applying the inverse function to the projection data.

Advantageous Effects of Invention

According to the invention, since measured data can be restored from projection data with high accuracy, system noise included in the restored measured data can be removed, and thus it is possible to improve image quality.

Hereinafter, an X-ray CT apparatus of embodiments of the invention will be described with reference to the drawings.

Figure 1:
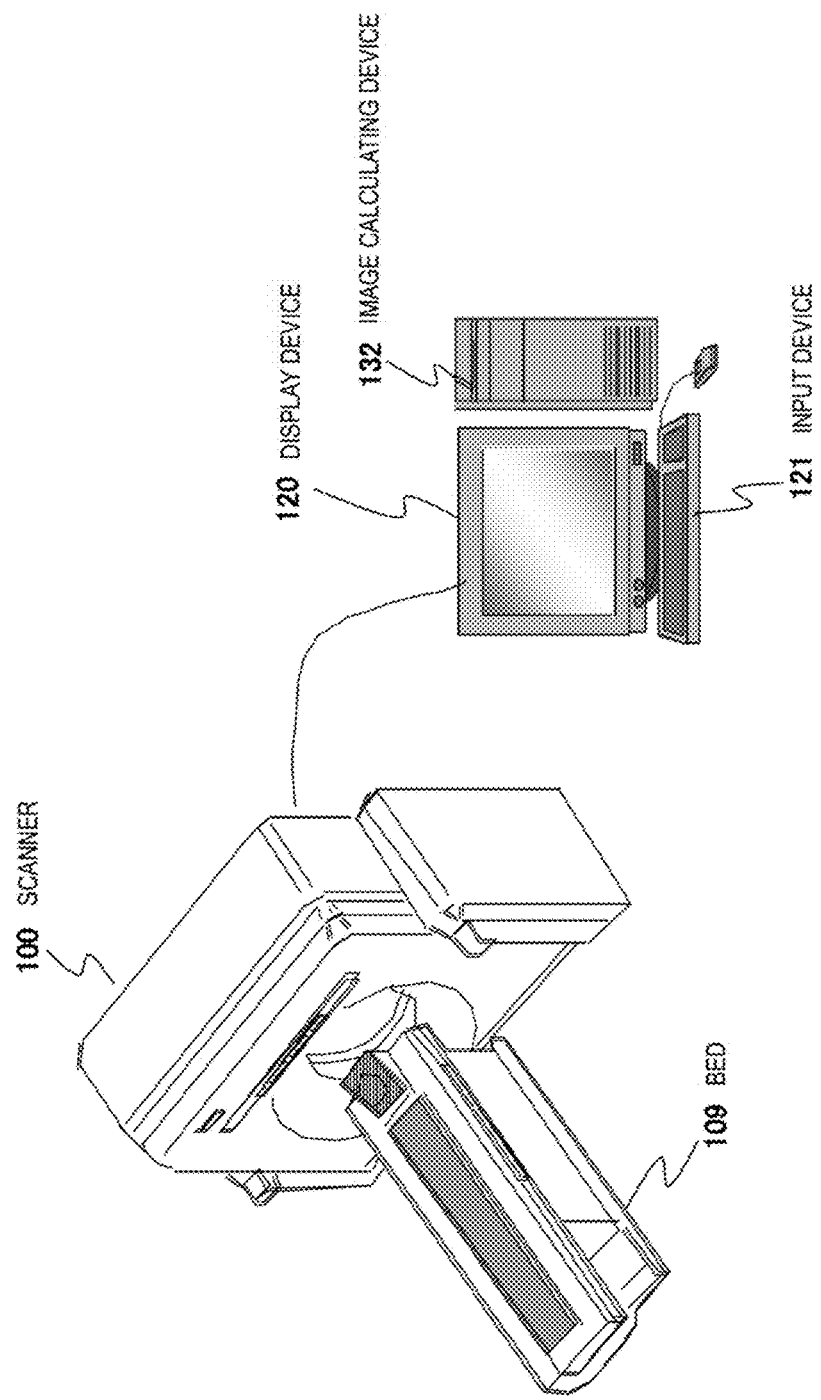
FIG. 1 is the entire schematic diagram of an X-ray CT apparatus of Embodiment 1.
Figure 2:
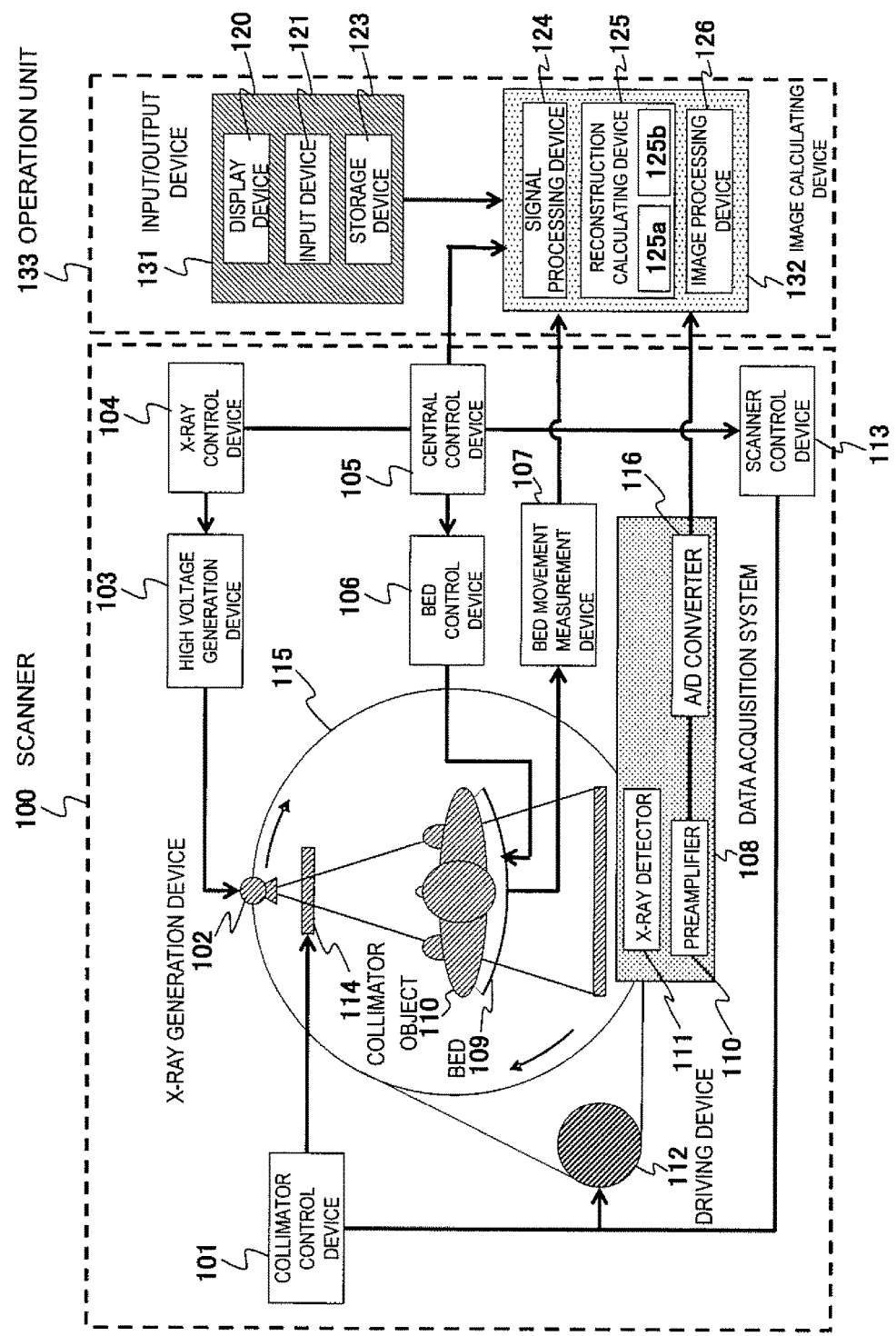
FIG. 2 is a block diagram illustrating a configuration of the X-ray CT apparatus of Embodiment 1.

The X-ray CT apparatus of the present embodiment is configured to include, as illustrated in FIGS. 1 and 2, an X-ray generation device 102 which irradiates an object 110 with X-ray, a data acquisition system 108 which detects X-rays having been transmitted through the object 110, a signal processing device 124, and a reconstruction calculating device 125. The signal processing device 124 processes an output signal from the data acquisition system 108 so as to obtain measured data including a signal value of 0 or less, and performs a conversion process on the measured data by using a predefined function including a logarithmic function so as to generate projection data. The reconstruction calculating device 125 performs a reconstruction process on the projection data so as to generate an image.

The predefined function is a function in which an inverse function is present for a value of a predetermined negative number or more. Therefore, measured data including signal values of 0 or less within a predetermined range is restored by applying the inverse function to projection data.

As mentioned above, in the invention, since the measured data can be restored from the projection data with high accuracy, so as to also include a predetermined range of 0 or less, system noise included in the restored measured data can be removed.

Hereinafter, embodiments of the invention will be described in detail.

<Embodiment 1>

Figure 3:
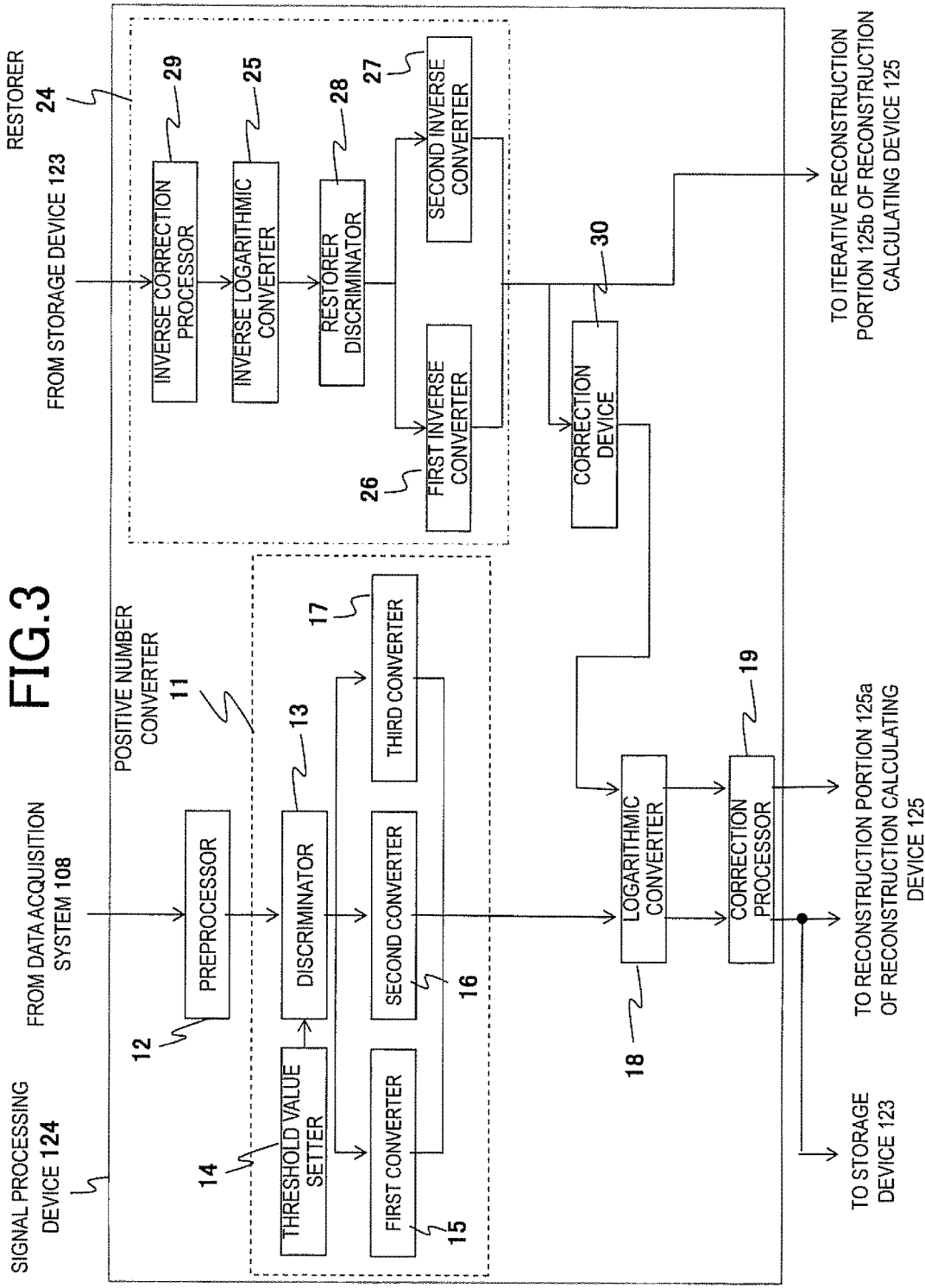
FIG. 3 is a block diagram illustrating a configuration of a signal processing device 124 of the X-ray CT apparatus of Embodiment 1.

In an X-ray CT apparatus of Embodiment 1, the signal processing device 124 includes a positive number converter 11 and a logarithmic converter 18 as illustrated in FIG. 3. The positive number converter 11 converts negative number data of measured data into positive number data by using a predefined positive number conversion function. The logarithmic converter 18 performs logarithmic conversion on the positive number data converted in the positive number converter 11 so as to generate projection data. The positive number conversion function of the positive number converter 11 is a function which monotonically increases for negative numbers within a predetermined range. If the monotonically increasing function is used as the positive number conversion function, it is possible to restore measured data of signal values of 0 or less within a predetermined range from the projection data by using an inverse function of the monotonically increasing function.

The X-ray CT apparatus of Embodiment 1 is preferably provided with a storage device 123 which stores the generated projection data, and the signal processing device 124 is preferably provided with a restorer 24 which reads the projection data stored in the storage device 123, and restores measured data including signal values of 0 or less within a predetermined range. The signal processing device 124 is preferably further provided with a correction device 30 which performs correction on the measured data restored by the restorer 24. Consequently, system noise included in the restored measured data can be removed by the correction device 30.

The reconstruction calculating device 125 is preferably provided with an iterative reconstruction portion 125b which performs iterative image reconstruction on the measured data restored by the restorer 24 so as to generate an image.

Figure 4:
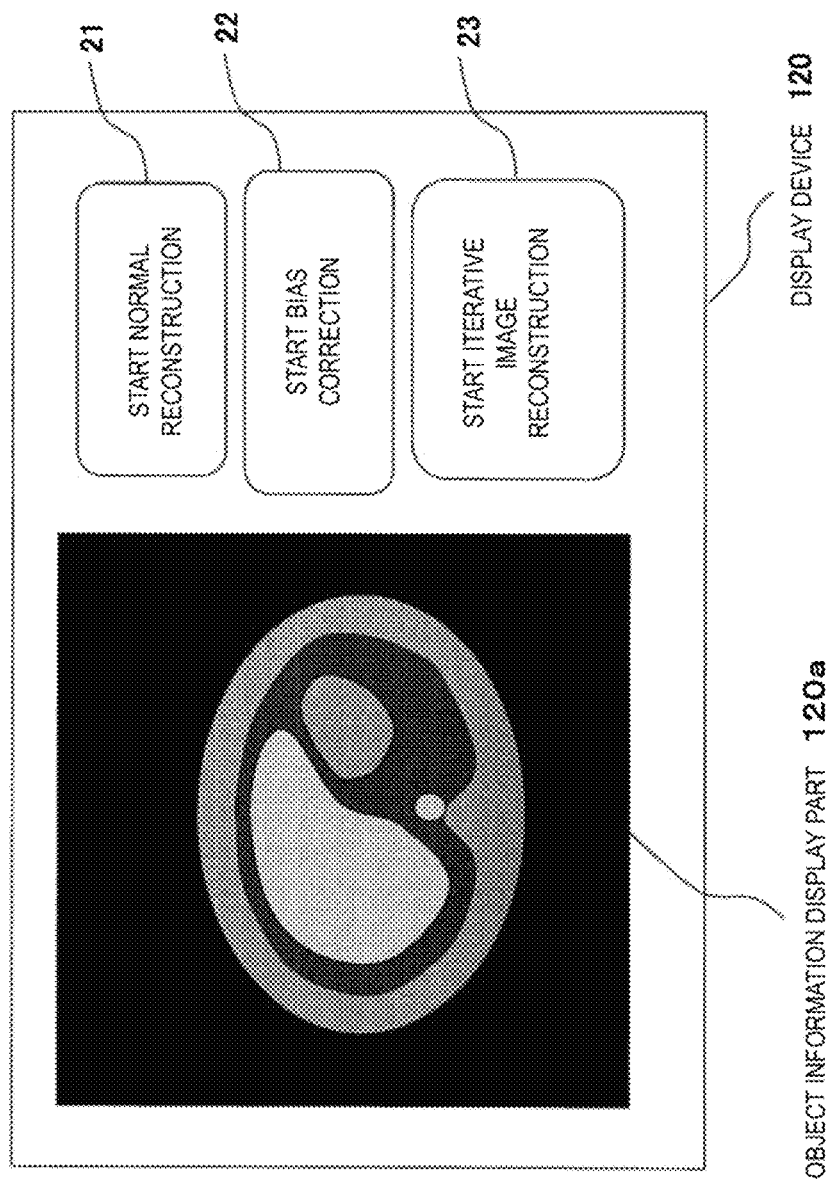
FIG. 4 is an explanatory diagram illustrating a display screen example of a display device 120 in Embodiment 1.

The X-ray CT apparatus of Embodiment 1 is preferably provided with an input device 121 which receives selection of normal image reconstruction and image reconstruction using measured data restored by the restorer 24, from an operator. The input device 121 may display a screen for receiving selection on a display screen of the display device 120 so as to receive the selection, for example, as illustrated in FIG. 4. In a case where the selection received by the input device 121 is the image reconstruction using measured data restored by the restorer 24, the signal processing device 124 performs restoration of the projection data stored in the storage device 123 by using the restorer 24.

Hereinafter, the X-ray CT apparatus of Embodiment 1 will be described in more detail.

FIG. 1 illustrates an exterior of the X-ray CT apparatus of the embodiment, and FIG. 2 is a block diagram illustrating an internal configuration of the X-ray CT apparatus. The X-ray CT apparatus includes a scanner 100 used for scanning, a bed 109 which moves the object placed thereon, the input device 121, an image calculating device 132, and the display device 120.

The image calculating device 132 includes the signal processing device 124 which processes data obtained by the data acquisition system 108, the reconstruction calculating device 125, and an image processing device 126. The input device 121 and the display device 120 constitute an input/output device 131 along with the storage device 123.

The input/output device 131 and the image calculating device 132 constitute an operation unit 133.

The scanner 100 includes the X-ray generation device 102, the data acquisition system 108, a collimator 114, and a rotation body 115 which is mounted with the above-described elements and is rotated around the object 110. The data acquisition system 108 includes an X-ray detector 111, a preamplifier 110, and an A/D converter 116. The scanner 100 is provided with a driving device 112 which rotationally drives the rotation body 115, a high voltage generation device 103, an X-ray control device 104, a scanner control device 113, a central control device 105, a bed control device 106, a bed movement measurement device 107, a collimator control device 101, and the like.

The input device 121 of the operation unit 133 is constituted of a mouse, a keyboard, and the like. The input device receives, from the operator, inputs of scanning conditions (a bed movement speed, a tube current, a tube voltage, a slice position, and the like), reconstruction parameters (a region of interest, a reconstructed image size, an inverse projection phase width, a reconstruction filter function, and the like), or selection of measured data used for image reconstruction. The display device 120 displays a reconstructed image, a screen for receiving inputs on the input device 121, and the like.

A description will be made of an operation of the scanner 100 during scanning. The central control device 105 sends control signals necessary in scanning to the X-ray control device 104, the bed control device 106, and the scanner control device 113 on the basis of scanning conditions received by the input device 121. Then, if the operator operates a scanning starting button, the X-ray control device 104, the bed control device 106, and the scanner control device 113 receive a scanning starting signal, and start operations for scanning.

The X-ray control device 104 outputs a control signal to the high voltage generation device 103. The high voltage generation device 103 applies a high voltage to the X-ray generation device 102 in response to the control signal. The X-ray generation device 102 irradiates the object 110 with X-rays.

Simultaneously, the scanner control device 113 outputs a control signal to the driving device 112. The driving device 112 rotates the rotation body 115 mounted with the X-ray generation device 102, the X-ray detector 111, the preamplifier 110, and the like, around the object 110. On the other hand, the bed control device 106 controls an operation of the bed 109 on which the object is placed, so as to stop or move the bed 109 in a body axis direction.

The X-rays emitted from the X-ray generation device 102 are restricted in an irradiation region by the collimator 114 so as to be applied to the object 110, pass through the object 110 while being absorbed (attenuated) by each tissue of the object 110, and are detected by the X-ray detector 111 of the data acquisition system 108. The X-ray detector 111 includes a plurality of detection elements which are arranged in two-dimensional directions (a channel direction and a column direction which is orthogonal thereto). Detection of a signal in the X-ray detector 111 is performed at discrete positions (views) in a rotation direction of the rotation body 115. A detection signal in the X-ray detector 111 is converted into a current so as to be amplified in the preamplifier 110, and is then converted into a digital signal in the A/D converter 116 so as to be output to the signal processing device 124.

With reference to FIG. 3, a description will be made of a configuration and an operation of the signal processing device 124. The signal processing device 124 is configured to include a preprocessor 12, the positive number converter 11, the logarithmic converter 18, a correction processor 19, the restorer 24, and the correction device 30. The preprocessor 12 performs a predetermined preprocess on an output signal from the data acquisition system 108 so as to obtain measured data x. The positive number converter 11 converts negative number data of the measured data x into positive number data y (=ϕ(x)) by using a predefined positive number conversion function ϕ(x). An example of the positive number conversion function ϕ(x) is shown in Equation (1).

[Expression 1]

$$y = \phi(x) = \begin{cases} x & (x \geq t) \\ \dfrac{1}{(s-t)^2}\left\{ (L-s)x^2 + (s^2 + t^2 - 2Lt)x + (L-s)t^2 \right\} & (s \leq x < t) \\ L & (x < s) \end{cases} \quad (1)$$

In the above Equation (1), the lower threshold value s (<0), the upper threshold values t (>0), and L (>0) are respectively any constants. However, the upper threshold value t satisfies a condition of t≥2L−s.

Figure 5:
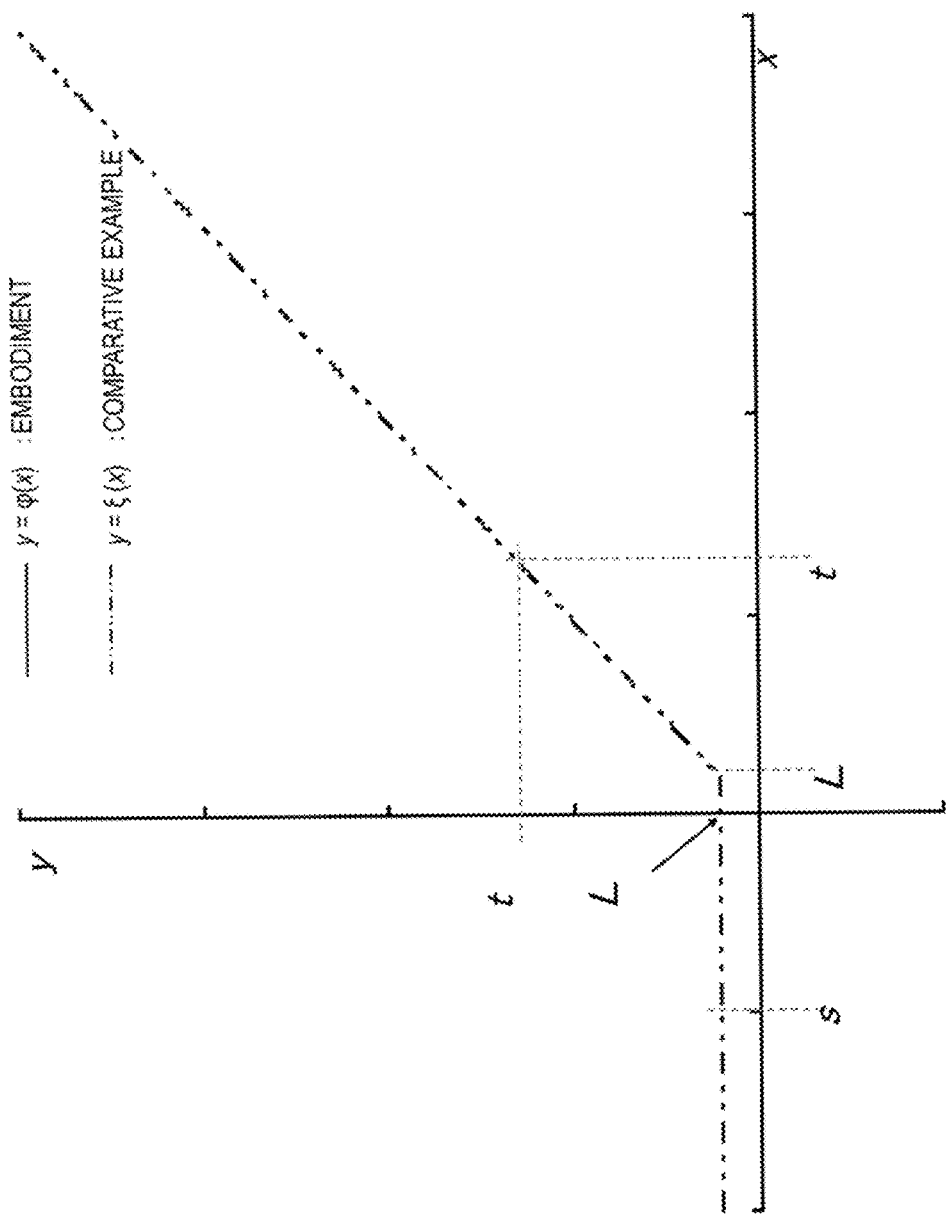
FIG. 5 is a graph illustrating a conversion function $\phi(x)$ used to convert measured data x into positive number data y in Embodiment 1.

A graph of the function ϕ(x) of Equation (1) is indicated by a solid line in FIG. 5. As illustrated in FIG. 5, a value y of the conversion function ϕ(x) takes a value of L or more, and linearly increases in a range of x≥t. Y=ϕ(x) is a function whose slope is larger than 0 in a range of s≤x≤t, and y and x correspond to each other on one-to-one basis. Therefore, ϕ(x) has an inverse function in a range of s≤x in which the variable x takes a negative number, and thus inverse conversion can be performed. As a result, the measured data x can be restored from the positive number data y in the range of s≤x.

ϕ(x) takes a constant value, for example, a value of L in a range of s≥x.

The logarithmic converter 18 applies a conversion function ρ(y) to the positive number data y converted by the positive number converter 11, so as to generate logarithmically converted data z. An example of the conversion function ρ(y) is shown in Equation (2).

[Expression 2]

$$z = \rho(y) = q - g\ln(y) \quad (2)$$

In Equation (2), q and g are positive numbers, and are constants determined according to a size of a storage region of the storage device 123 storing projection data a and desired accuracy for the projection data a.

The correction processor 19 performs a predetermined correction process on the logarithmically converted data z so as to obtain the projection data a which is then output to the reconstruction calculating device 125 and is also output to the storage device 123 so as to be stored. The restorer 24 reads the projection data a stored in the storage device 123, and restores the measured data x including signal values of 0 or less within a predetermined range. The correction device 30 performs a predetermined correction process such as bias correction on the restored measured data x, so as to reduce system noise included in the measured data x. The measured data from which the system noise is reduced is input to the logarithmic converter 18.

The positive number converter 11 is configured to include a discriminator 13, a threshold value setter 14, and first, second and third converters 15, 16 and 17. The threshold value setter 14 holds the threshold values s, t and L used for the functions ϕ(x) and ρ(y). The threshold value s is a negative number, and t is a positive number. The threshold values s, t and L may be changed to any values by the operator operating the input device 121. There may be a configuration in which a variance value σ of system noise specific to the X-ray CT apparatus system is measured by the signal processing device 124, and s and t are calculated on the basis of the variance value σ.

This calculation method will be described later.

The discriminator 13 reads the threshold values s, t and L from the threshold value setter 14, and distributes the measured data x output from the preprocessor 12 to the first, second and third converters 15, 16 and 17. The first converter 15 receives the measured data x which is equal to or more than the threshold value t illustrated in FIG. 5, and outputs the input signal as the positive number data y as it is. The second converter 16 receives the measured data x which is less than the threshold value t and is equal to or more than the threshold value s, and generates and outputs the positive number data y by converting the measured data x into a positive number by using the function ϕ(x). The third converter 17 receives the measured data x which is less than the threshold value s so as to convert the measured data x into the fixed data value L, and outputs the data value as the positive number data y.

On the other hand, the restorer 24 includes an inverse correction processor 29, an inverse logarithmic converter 25, a restorer discriminator 28, a first inverse converter 26, and a second inverse converter 27. The inverse correction processor 29 applies an inverse process of the process in the correction processor 19 to the projection data a stored in the storage device 123, so as to restore the logarithmically converted data z. The inverse logarithmic converter 25 converts the restored logarithmically converted data z by using an inverse function of the conversion function ρ(y) so as to restore the positive number data y. The restorer discriminator 28 reads t and L from the threshold value setter 14, and distributes the restored positive number data y to the first and second inverse converters 26 and 27. The first inverse converter 26 receives the positive number data y which is equal to or more than the threshold value t, and outputs the input signal as the measured data x as it is.

The second inverse converter 27 receives the positive number data y which is more than the threshold value L and is less than the threshold value t, and outputs the positive number data y as the measured data x by converting the positive number data into the measured data by using an inverse function of the conversion function ϕ(x) used in the second converter 16. Consequently, it is possible to restore the measured data x corresponding to the positive number data y which is more than the threshold value L. Therefore, the measured data x is restored even in the negative number range of s<x<0. The correction device 30 performs a bias correction process or the like on the restored measured data x so as to remove system noise therefrom. The restored measured data x from which the system noise is removed is input to the logarithmic converter 18 so as to be subjected to logarithmic conversion, and undergoes a correction process in the correction processor 19, and thus projection data b is obtained.

The reconstruction calculating device 125 includes a reconstruction portion 125a which reconstructs an image on the basis of the projection data a and b from the correction processor 19, and an iterative reconstruction portion 125b which generates an image through an iterative image reconstruction process on the basis of the measured data x output from the restorer 24. The restored projection data b is generated from the measured data x from which the system noise is removed, unlike the projection data a which is rapidly generated without removing the system noise, and is thus subjected to a reconstruction process in the reconstruction portion 125a, so that an image from which artifacts caused by the system noise are removed can be generated. The restored measured data x is subjected to an iterative image reconstruction process in the iterative reconstruction portion 125b, and thus an image from which artifacts caused by the system noise are removed can be generated.

The reconstructed image is preserved in the storage device 123 of the input/output device 131, and is displayed as a CT image on the display device 120. The image processing device 126 performs image processing on the reconstructed image in response to the operator's operation.

Hereinafter, a further description will be made of an operation of the image calculating device 132 of the present embodiment with reference to a processing flowchart and the like.

First, the signal processing device 124 displays a selection reception screen as illustrated in FIG. 4 on the display device 120 in order to receive selection of a processing mode from the operator. The selection reception screen includes an object information display part 120a for displaying an image of the object 110, projection data, or information such as scanning conditions, an icon 21 for receiving an instruction for starting normal reconstruction, an icon 22 for receiving an instruction for reconstruction after bias correction is performed on the measured data x, and an icon 23 for receiving an instruction for iterative reconstruction based on the measured data x. The operator operates the input device 121 so as to select any one of the icons 21 to 23, and thus selects a processing mode.

Also in a case where an image is reconstructed again by changing reconstruction conditions, on the basis of projection data obtained through previous scanning, the projection data a preserved in the storage device 123 is specified, and any one of the icons 21 to 23 is selected, so that a desired process is performed.

Figure 6:
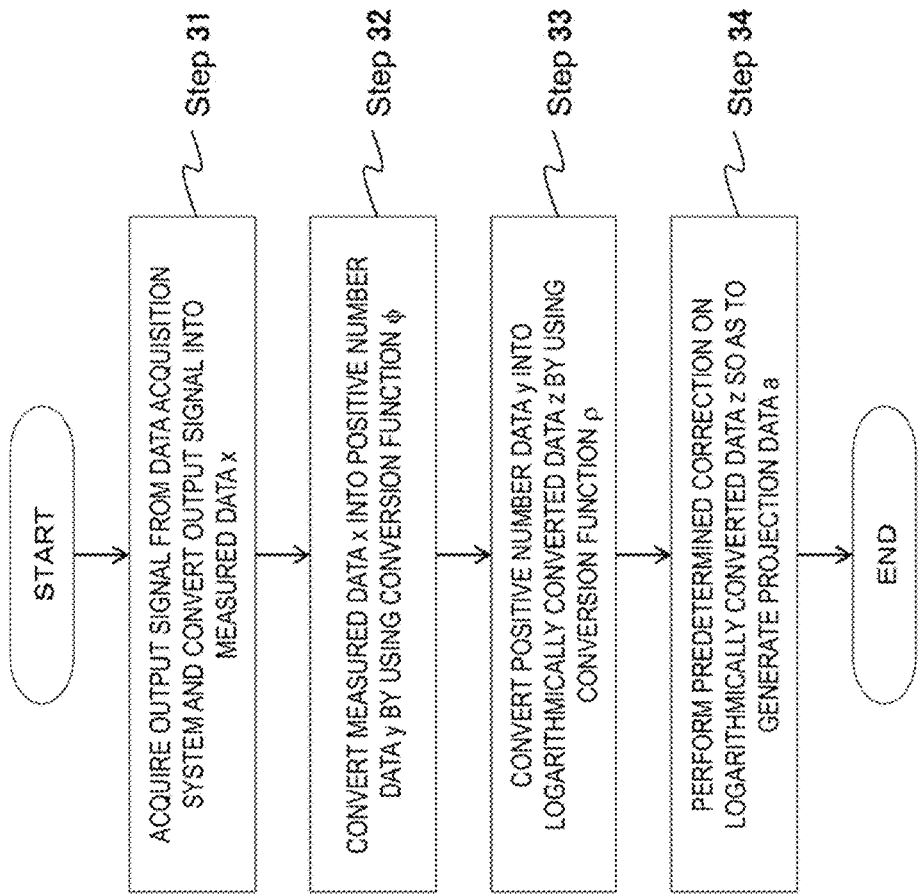
FIG. 6 is a flowchart illustrating an operation in which the signal processing device 124 of Embodiment 1 converts an output signal from a data acquisition system 108 into projection data.

In a case where the operator selects the icon 21 so as to give an instruction for starting the normal reconstruction, the signal processing device 124 acquires an output signal from the data acquisition system 108 so as to perform processes as in Steps 31 to 34 in FIG. 6.

First, in Step 31, the preprocessor 12 restores the signal acquired from the data acquisition system 108 to an original number of bits in a case where the signal is compressed for transmission. Signal value correction is performed in which an output signal in a state in which X-rays are not applied is subtracted from the data restored to the original number of bits, and thus the measured data x is obtained.

Next, in Step 32, the positive number converter 11 converts the measured data x into restorable positive number data y by using the above-described conversion, function ϕ(x). In the present invention, as illustrated in FIG. 5, a function is used in which the negative lower threshold value s is provided in the domain, and the argument x of the conversion function ϕ and a value y (=ϕ(x)) thereof correspond to each other on one-to-one basis in the domain which is equal to or less than 0 and is equal to or more than the lower threshold value s.

The discriminator 13 reads the threshold values s, t and L from the threshold value setter 14, and distributes the measured data x output from the preprocessor 12 to the first, second and third converters 15, 16 and 17 according to the function ϕ(x) of Equation (1). The first converter 15 receives the measured data x of x≥t, and outputs the measured data as the positive number data y as it is according to y=x of the function ϕ(x). The second converter 16 receives the measured data x of s≤x≤t, and generates and outputs the positive number data y by using the function ϕ(x) in above Equation (1). The third converter 17 receives the measured data x of x<s so as to convert all the measured data into L according to the function ϕ(x), and outputs L as the positive number data y.

Here, values of t, s, and L in the above Equation (1) will be described. In a case of x≥t, there is no reduction in the accuracy of data due to conversion and inverse conversion, and thus t is preferably small. However, in order for the argument x and the value ϕ(x) thereof to correspond to each other on one-to-one basis, ϕ(x) is required to be a monotonically increasing function in a narrow sense in the range of s≤x≤t. The monotonically increasing function preferably continues at y=ϕ(x) and x=t in a case of x≥t.

Thus, a condition of 2L−s≤t is derived, and it is possible to make a range of a reduction in the data accuracy narrowest at 2L−s=t. Therefore, t is a value defined by s, and, thus, as a value of s becomes greater, data can be converted with higher accuracy. On the other hand, the measured data x with a value smaller than s is rounded up to L according to the conversion function ϕ(x). Therefore, as a value of s becomes smaller, the measured data x which is rounded up to L according to the conversion function ϕ(x) becomes less.

In other words, s is a parameter for adjusting an upper limit value for maintaining the data accuracy, and a lower limit value of data which is rounded up. The operator may set any s and t so that the condition of t≥2L−s is satisfied. Any value of L satisfying a condition described in Step 33 in FIG. 6 is set.

A value of s may be set through computation on the basis of a variance of the measured data x.

The measured data x takes a value of 0 less due to system noise. The system noise can be generally modeled according to normal distribution, and has an average value of 0 and a variance value σ which depends on the data acquisition system 108.

The variance value σ may be calculated experimentally, through simulation, or the like. Therefore, if s is set to correspond to the variance value σ, s which is small more than necessary is not set, and thus a ratio of data to be rounded up can be reduced. For example, in normal distribution of the variance $σ^2$ of system noise, it is known that about 68% of the entire data is present in the range of σ, and about 95% thereof is present in the range of 2σ. Therefore, for example, s is set according to Equation (3), and thus it is possible to reduce a ratio of the measured data x which is rounded up to L by using the conversion function ϕ(x). As a result of taking into consideration the capacity of the storage region of the storage device 123 storing the projection data a and the data accuracy, κ is preferably experimentally set to be equal to or less than 6.

[Expression 3]

$$s = κσ (0 < ∀κ ≤ 6) \quad (3)$$

In relation to the conversion function ϕ(x) in the range of s≤x≤t in Equation (1), the coefficients are calculated in advance on the basis of s and L, and thus conversion can be performed without causing a large amount of computation.

As a comparative example, first, a conversion function ξ(x) of the related art is shown in Equation (4). A graph of Equation (4) is indicated by a dot chain line in FIG. 5.

[Expression 4]

$$\xi(x) = \begin{cases} x & (x \geq L) \\ L & (x < L) \end{cases} \quad (4)$$

Here, L (>0) is any constant.

As in Equation (4), in the related art, the measured data x of x<L is rounded up to the positive number L according to ξ(x). ξ(x) (=y) at x<L does not correspond to x on one-to-one basis, and thus an inverse function thereof is not present. Therefore, the measured data x cannot be restored from the positive number data y by using an inverse function of ξ(x).

Next, in Step 33, the converted signal y calculated in Step 32 is logarithmically converted by using the logarithmic function ρ(y) of Equation (2), and thus logarithmically converted data z is obtained.

Here, a description will be made of a method of determining q and g in Equation (2). The maximum value of the projection data a is a value obtained by the correction processor 19 performing correction on the maximum value r of the logarithmically converted data z expressed by Equation (5).

[Expression 5]

$$r = q - g\ln(L) \quad (5)$$

Preferably, q of Equation (2) is experimentally set so that a value (the maximum value of the projection data a) obtained by the correction processor 19 performing correction on r of Equation (5) in the next Step 34 falls within an upper limit (for example, an upper limit of a 16-bit signed integer) of the storage region of the projection data a of the storage device 123. In addition, g of Equation (2) is experimentally set on the basis of a range of values and the accuracy of a CT image which is reconstructed from the projection data a. Further, L is experimentally set as a lower limit value of valid positive number data y on the basis of a range of the projection data a corresponding to r. One of the effects of the invention is that a lower threshold value of measured data which can be restored after logarithmic conversion can be extended from the positive number L of the related art to the negative number s while maintaining the maximum value r of the logarithmically converted data z.

Figure 7:
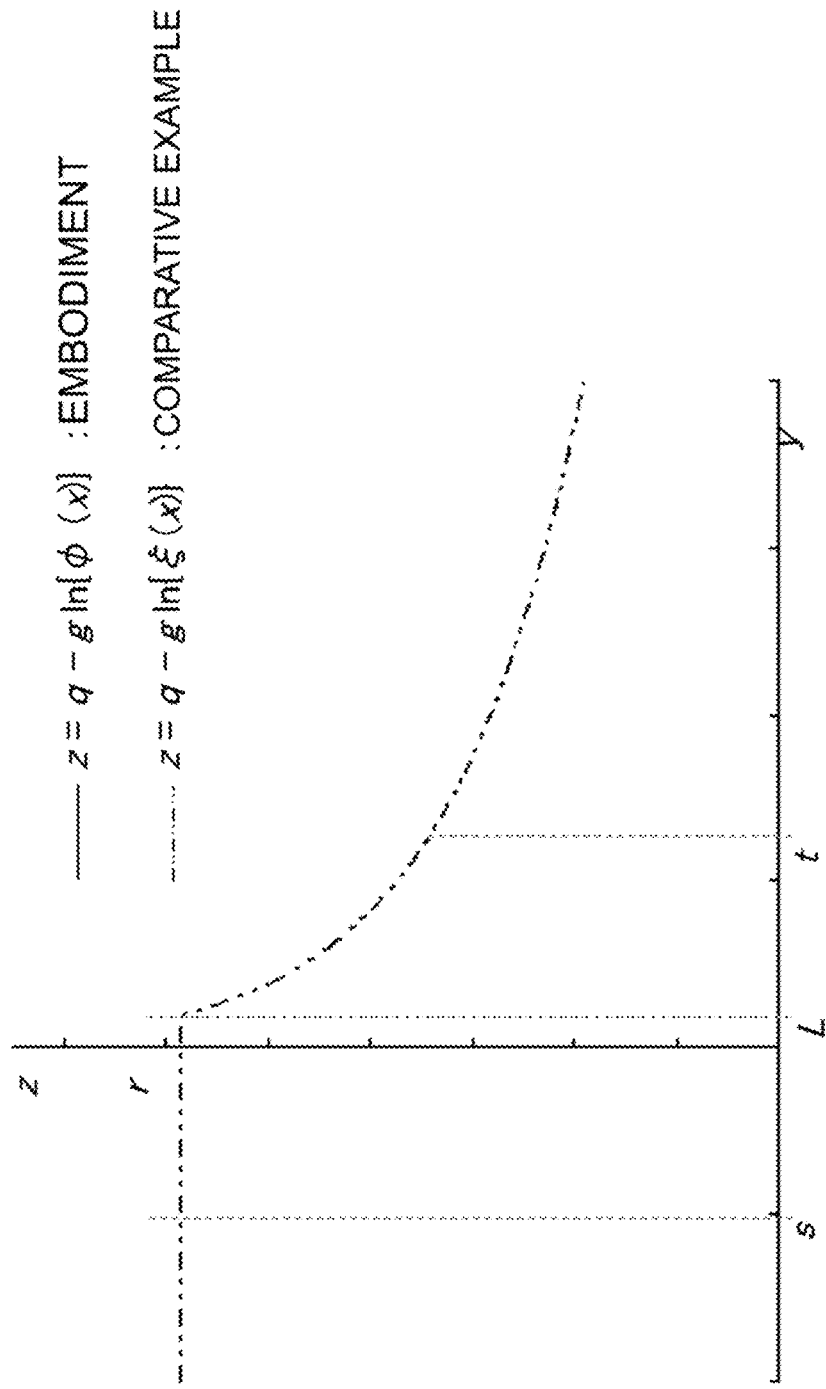
FIG. 7 is a graph illustrating logarithmically converted data z in Embodiment 1.

The logarithmically converted data z generated in Step 33 is indicated by a solid line graph in FIG. 7. The conversion function ξ(x) of the related art is used as a comparative example in Step 32, and logarithmically converted data obtained in the same manner as in the present embodiment in Step 33 is indicated by a dot chain line graph in FIG. 7. In both of the present embodiment and the comparative example, the logarithmically converted data is a function having r as the maximum value, and sizes of the projection data a are the same as each other. However, in a case where each inverse function is considered, since the logarithmically converted data z of the comparative example entirely has the value of r in the range of x<L, an inverse function thereof is not present, and thus a value of the measured data x cannot be restored. In contrast, it can be seen that the logarithmically converted data z of the present embodiment is a monotonically decreasing function even in the range of s≤x<L, an inverse function thereof is present, and thus a value of the measured data x can be restored.

In Step 34, reference correction using values in a reference detector, air correction using data obtained through scanning when there is no object 110, phantom correction for suppressing a beam hardening effect, and the like are performed on the logarithmically converted data z obtained in Step 33, so that the projection data a is obtained. The projection data a is preserved in the storage device 123 of the input/output device 131. The values in the reference detector used in various correction, the data obtained through scanning when there is no object 110, and parameters of functions used for the phantom correction are also preserved in the storage device 123 of the input/output device 131.

Next, with reference to FIG. 8, a description will be made of operations of the reconstruction calculating device 125 and the signal processing device 124. The reconstruction calculating device 125 acquires the projection data a from the storage device 123 (Step 61), and checks a processing mode which is selected by the operator via the input device 121 by using the screen illustrated in FIG. 4. Here, since the operator selects the icon 21 so as to give an instruction for starting normal reconstruction, the reconstruction calculating device 125 reconstructs an image of the object 110 by using the reconstruction portion 125a (Step 63). The reconstructed image is displayed on the object information display part 120a of the display device 120 illustrated in FIG. 4.

In the above-described Steps 31 to 34 of generating the projection data a and Steps 61 to 63 of generating an image through normal reconstruction, a process of removing system noise is not performed, and thus an image of the object 110 can be generated within a short period of time. Therefore, this is suitable in a case where rapid image display is necessary such as a case of an emergency patient.

On the other hand, through the above Steps 31 to 34, the projection data a is stored in the storage device 123, and thus it is possible to perform the process or reducing system noise by using the projection data a. Consequently, it is possible to perform the processing mode for qenerating a highly accurate image with reduced artifacts. This will now be described.

If the projection data a is stored in the storage device 123, the operator can select the icon 22 for giving an instruction for performing image reconstruction by using measured data from which system noise is reduced through bias correction, or the icon 23 for giving an instruction for reconstructing an image from which artifacts due to system noise are reduced by performing iterative image reconstruction based on the measured data, on the display screen illustrated in FIG. 4. The operator checks an image on the object information display part 120a, and selects the icon 22 or 23 as necessary.

Figure 8:
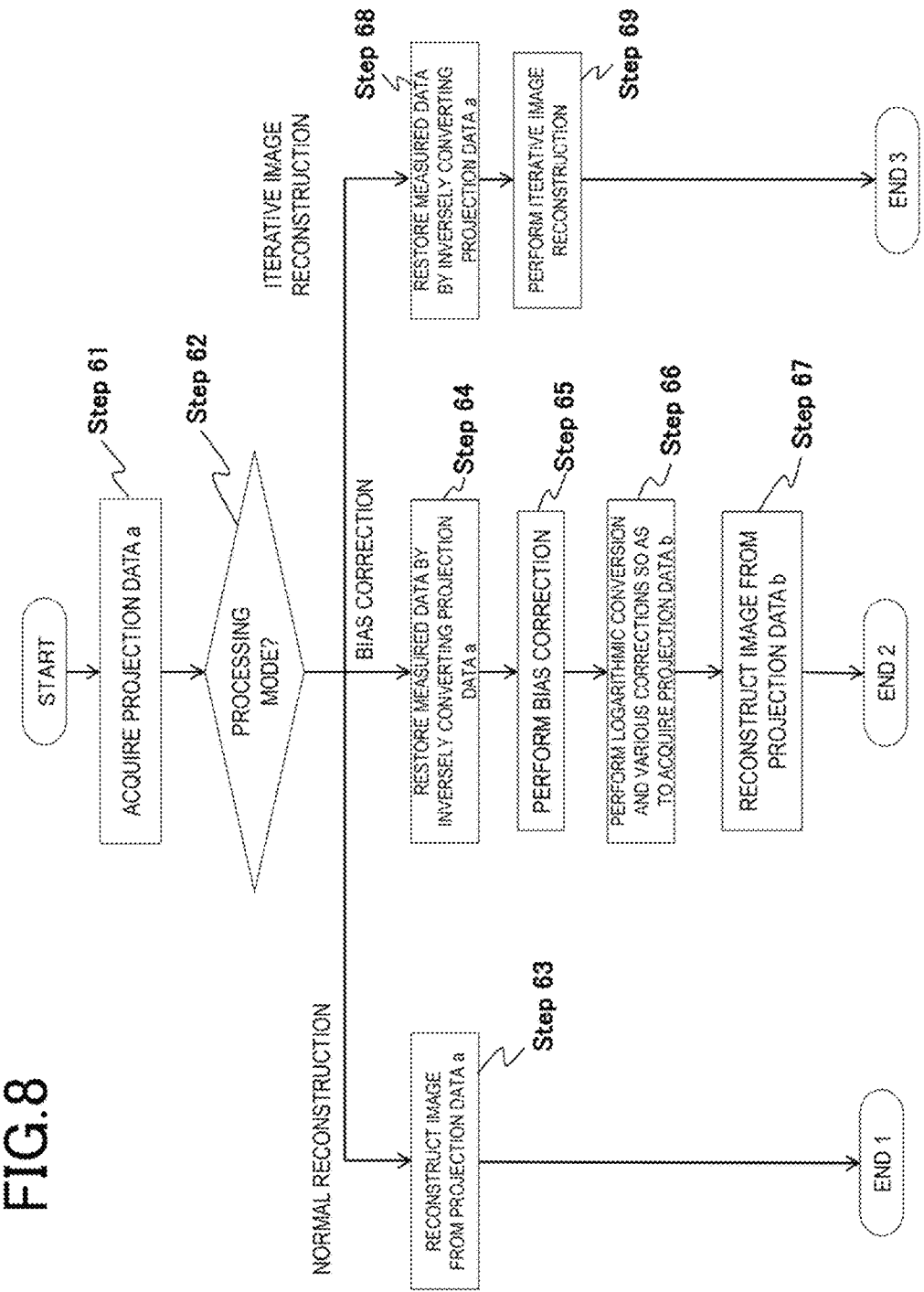
FIG. 8 is a flowchart illustrating an image reconstruction operation of the signal processing device 124 and a reconstruction calculating device 125 of Embodiment 1.

The reconstruction calculating device 125 checks a processing mode in Step 62 in FIG. 8, and instructs the restorer 24 of the signal processing device 124 to restore the measured data x from the projection data a in a case where the icon 22 for giving an instruction for bias correction is selected. The restorer restores the measured data x (Step 64).

An operation of the restorer 24 will be described in detail with reference to FIG. 9. The inverse correction processor 29 of the restorer 24 performs a correction process inverse to the correction process in the correction processor 19 on the projection data a stored in the storage device 123, so as to restore the logarithmically converted data z (Step 121). The inverse logarithmic converter 25 converts the restored logarithmically converted data z by using an inverse function of the conversion function ρ(y), so as to restore the positive number data y (Step 122).

The restorer discriminator 28 reads t and L from the threshold value setter 14, and distributes the restored logarithmically converted data z to the first and second inverse converters 26 and 27. The first inverse converter 26 receives the positive number data y which is equal to or more than the threshold value t, and outputs the input signal as the measured data x as it is.

The second inverse converter 27 receives the positive number data y which is more than the threshold value L and is smaller than the threshold value t, and outputs as the measured data x as a result of converting by using an inverse function of the function φ(x) used in the second converter 16. Consequently, the measured data x is restored not only in the range of a positive number but also in the range of s<x≤0 (Step 123).

Next, the correction device 30 of the signal processing device 124 performs a bias correction process and the like on the restored measured data x so as to remove system noise therefrom (Step 65 in FIG. 8). The bias correction process is a method in which a value of measured data in a focused element of the detector 111 is corrected through iterative filtering processes while maintaining positivity of the focused element and an average value of the focused element and an adjacent element by referring to a value of measured data in the adjacent element of the focused element. The bias correction process is a well-known technique disclosed in the above NPL 1 or the like, and thus a detailed description thereof will be omitted here.

The measured data x from which the system noise is removed through the bias correction is input from the correction device 30 to the logarithmic converter 18, as illustrated in FIG. 3, is logarithmically converted, undergoes a correction process in the correction processor 19, and thus projection data b is obtained (Step 66).

The reconstruction calculating device 125 performs a reconstruction process on the projection data b by using the reconstruction portion 125*a*, so as to generate an image. Since the system noise is removed from the projection data b, an image with reduced artifacts due to the system noise can be obtained. The obtained image is displayed on the object information display part 120*a* of the display screen illustrated in FIG. 4.

On the other hand, the reconstruction calculating device 125 checks a processing mode in Step 62 in FIG. 8, and instructs the restorer 24 of the signal processing device 124 to restore the measured data x from the projection data a in a case where the icon 23 for giving an instruction for performing iterative reconstruction based on the measured data x is selected by the operator. The restorer 24 restores the measured data x (Step 68).

The operation in Step 68 is the same as that in Step 64 in the case of the bias correction, and thus description thereof will be omitted here. The restored measured data x is delivered to the iterative reconstruction portion 125*b* of the reconstruction calculating device 125, and an image is reconstructed by performing an iterative reconstruction process on the measured data x. Specifically, for example, models of the photon noise and the system noise included in the measured data are generated, and an image is calculated by using an iterative solution on the basis of the models. Because of this, an image reducing the influence of the system noise can be obtained. The iterative image reconstruction method is a well-known method disclosed in the above NPL 2, and thus a detailed description thereof will be omitted here. The obtained image is displayed on the object information display part 120*a* of the display screen illustrated in FIG. 4.

As mentioned above, in the invention, since an image with reduced system noise can be generated by restoring the measured data x from the projection data a projected onto the storage device 123, it is possible to realize both of rapid image display and highly accurate image display corresponding thereto without scanning the object 110 again. Therefore, in a case where rapid image display is necessary such as a case of an emergency patient, an image is generated through normal reconstruction in which a process of reducing system noise is not performed (Step 63), and, then, a highly accurate image may be generated and displayed by performing a process of reducing the system noise through bias correction, iterative image reconstruction, or the like, as necessary (Steps 64 to 67, and Steps 68 and 69).

In the above-described embodiment, a description has been made of a case where the projection data a corresponding to one image is stored in the storage device 123, but there may be a configuration in which projection data corresponding to a plurality of images is stored in the storage device 123. In this case, the image reconstruction device 125 acquires the projection data a corresponding to an image selected by the operator when the projection data a is acquired in Step 61 in FIG. 8. Consequently, the measured data x can be restored not only from the projection data a of a previously captured image but also from the projection data a of an image captured in the past, and thus an image with reduced system noise can be reconstructed.

<Embodiment 2>

An X-ray CT apparatus of Embodiment 2 will be described.

In the above-described Embodiment 1, there is a configuration in which the signal processing device 124 includes the positive number converter 11 and the logarithmic converter 18, converts the measured data x into the positive number data y by using the function φ(x), and then converts the positive number data into the logarithmically converted data z by using the function ρ(y), but the invention is not limited to this configuration. In Embodiment 2, the measured data x is converted into the logarithmically converted data z by using a single conversion function φ(x).

As the conversion function φ(x), for example, as shown in Equation (6), a function is used in which a conversion function for converting the measured data x into positive number data is provided in an argument of a logarithmic function.

[Expression 6]

$$z = \phi(x) = \begin{cases} q - g\ln(x) & (t \le x) \\ q - g\left\{\frac{1}{t}x + \ln(t) - 1\right\} & (s \le x < t) \\ r & (x < s) \end{cases} \quad (6)$$

In the above Equation (6), a lower threshold value s (<0) and upper threshold values t (>0) and L (>0) are respectively any constants.

Figure 10:
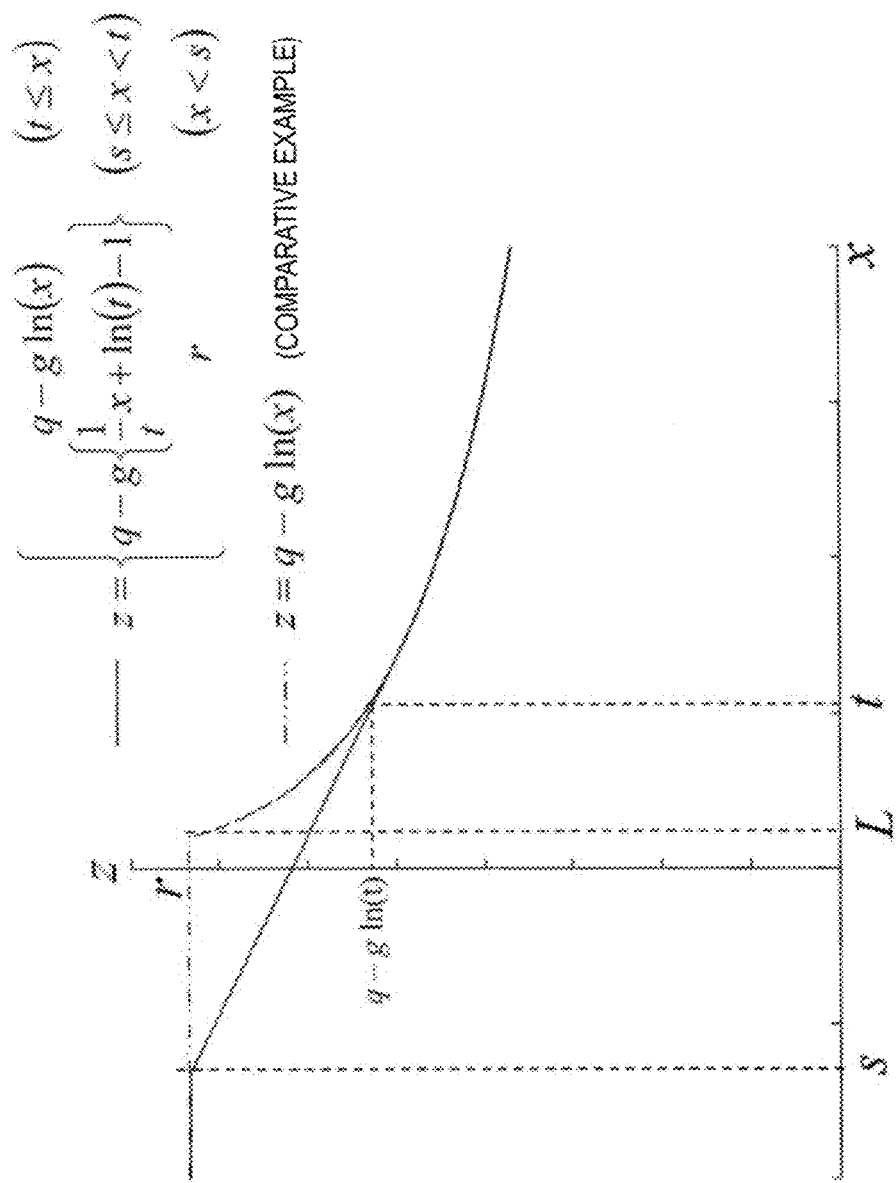
FIG. 10 is a graph illustrating logarithmically converted data z in Embodiment 2.

The conversion function φ(x) of Equation (6) is used to convert the measured data x into the logarithmically converted data z as indicated by a solid line graph in FIG. 10. As is clear from FIG. 10, in the range of the lower threshold value s or more, the argument x and a value of the conversion function z(=φ(x)) correspond to each other on one-to-one basis, and thus an inverse function thereof is present. Therefore, the measured data x can be restored from the logarithmically converted data z by using the inverse function.

Figure 11:
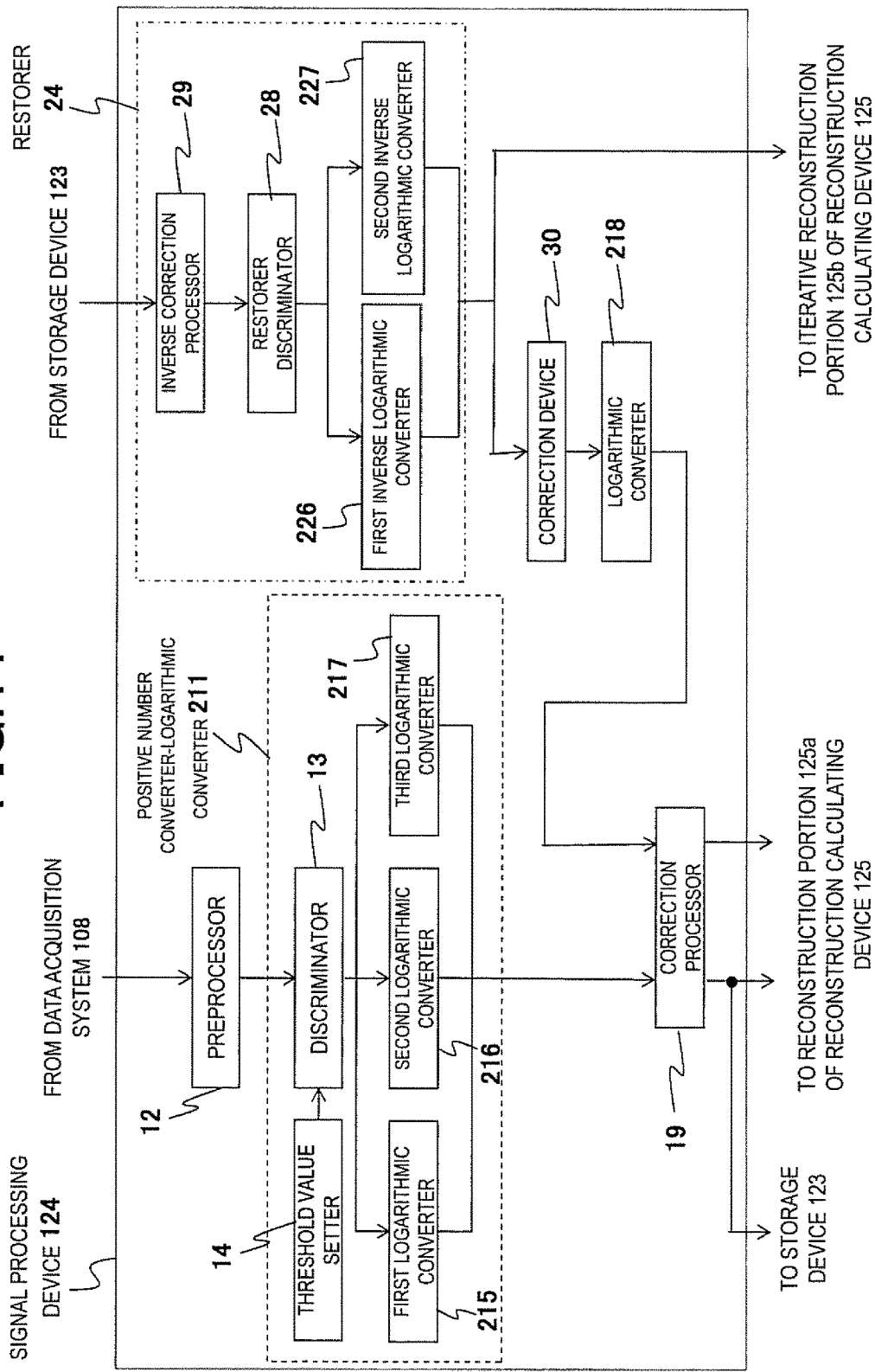
FIG. 11 is a block diagram illustrating a configuration of a signal processing device 124 of Embodiment 2.

FIG. 11 illustrates a configuration of the signal processing device 124 of the X-ray CT apparatus of Embodiment 2. As illustrated in FIG. 11, the signal processing device 124 of Embodiment 2 has the same configuration as that of the signal processing device illustrated in FIG. 3 in Embodiment 1, but includes a positive number converter/logarithmic converter 211 replacing the functions of the positive number converter 11 and the logarithmic converter 18 of Embodiment 1. The signal processing device 124 of Embodiment 2 is configured to include a preprocessor 12, a positive number converter/logarithmic converter 211, a correction processor 19, a restorer 24, a correction device 30, and a logarithmic converter 218. The logarithmic converter 218 is provided to logarithmically convert the measured data x restored by the restorer 24. The preprocessor 12, the correction processor 19, and the correction device 30 have the same configurations as those in Embodiment 1.

The positive number converter/logarithmic converter 211 is configured to include a discriminator 13, a threshold value setter 14, and first, second and third logarithmic converters 215, 216 and 217. The threshold value setter 14 holds the threshold values s, t and L in the same manner as in Embodiment 1. The discriminator 13 reads the threshold values s, t and L from the threshold value setter 14, and distributes the measured data x output from the preprocessor 12 to the first, second and third logarithmic converters 215, 216 and 217, in the same manner as in Embodiment 1.

The first logarithmic converter 215 receives the measured data x of t≤x illustrated in FIG. 10, and logarithmically converts the measured data by using the function φ(x) at t≤x in Equation (6) so as to output as the logarithmically converted data z. The second logarithmic converter 216 receives the measured data x of s≤x≤t, and performs both positive number conversion and logarithmic conversion on the measured data by using the function φ(x) at s≤x≤t in Equation (6) so as to output as the logarithmically converted data z. The third logarithmic converter 217 receives the measured data x of x<s, and converts all the measured data into r by using the function φ(x) in Equation (6) so as to output as the logarithmically converted data z. The correction processor 19 corrects the logarithmically converted data z so as to generate projection data a.

The restorer 24 includes an inverse correction processor 29, a restorer discriminator 28, a first inverse logarithmic converter 226, and a second inverse logarithmic converter 227. The inverse correction processor 29 restores the logarithmically converted data z from the projection data a in the same manner as in Embodiment 1. The restorer discriminator 28 reads t and L from the threshold value setter 14, and distributes the restored logarithmically converted data z to the first and second inverse logarithmic converters 226 and 227.

The first inverse logarithmic converter 226 receives the logarithmically converted data z of q-gln(t) or less, and converts the logarithmically converted data into the measured data x by using an inverse function of the function φ(x) used in the first logarithmic converter 215, so as to output as the measured data x. The second inverse logarithmic converter 227 receives the logarithmically converted data z of more than q-gln(t) and r or less, and converts the logarithmically converted data into the measured data x by using an inverse function of the function φ(x) used in the second converter 216, so as to output as the measured data x. Consequently, the measured data x is restored even in the negative number range of s<x<0. The correction device 30 performs a bias correction process or the like on the restored measured data x so as to remove system noise therefrom. The restored measured data x from which the system noise is removed is input to the logarithmic converter 218 so as to be subjected to logarithmic conversion, and undergoes a correction process in the correction processor 19, and thus projection data b is obtained.

Figure 12:
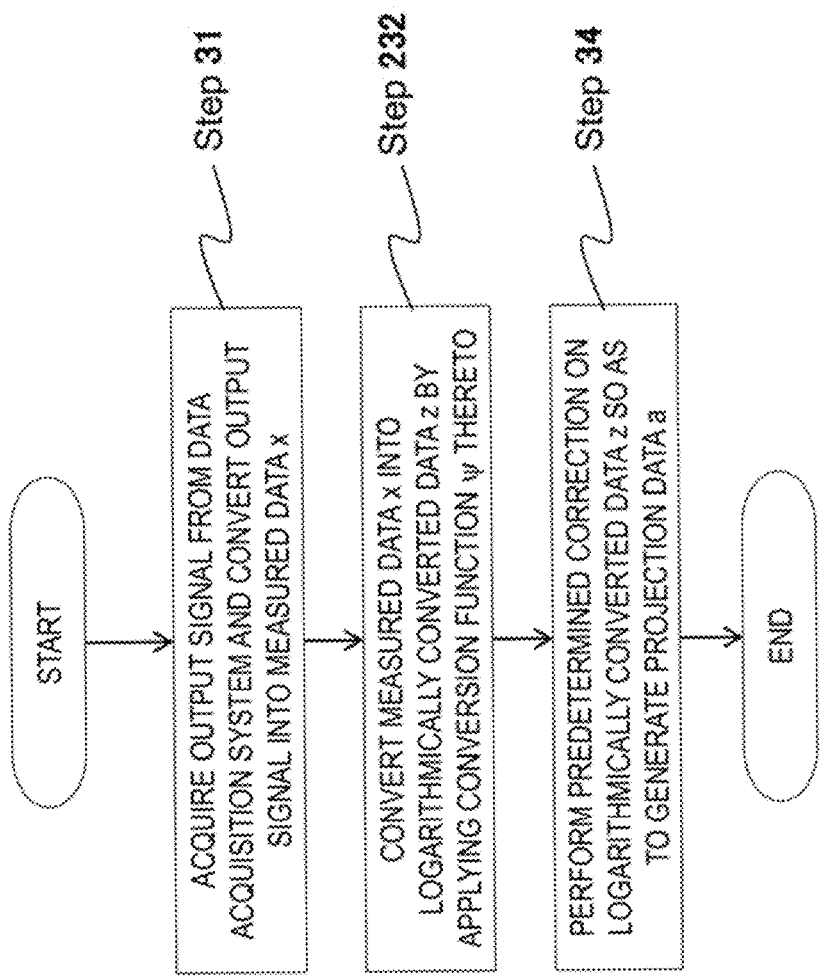
FIG. 12 is a flowchart illustrating an operation in which the signal processing device 124 of Embodiment 2 converts an output signal from a data acquisition system 108 into projection data.
Figure 13:
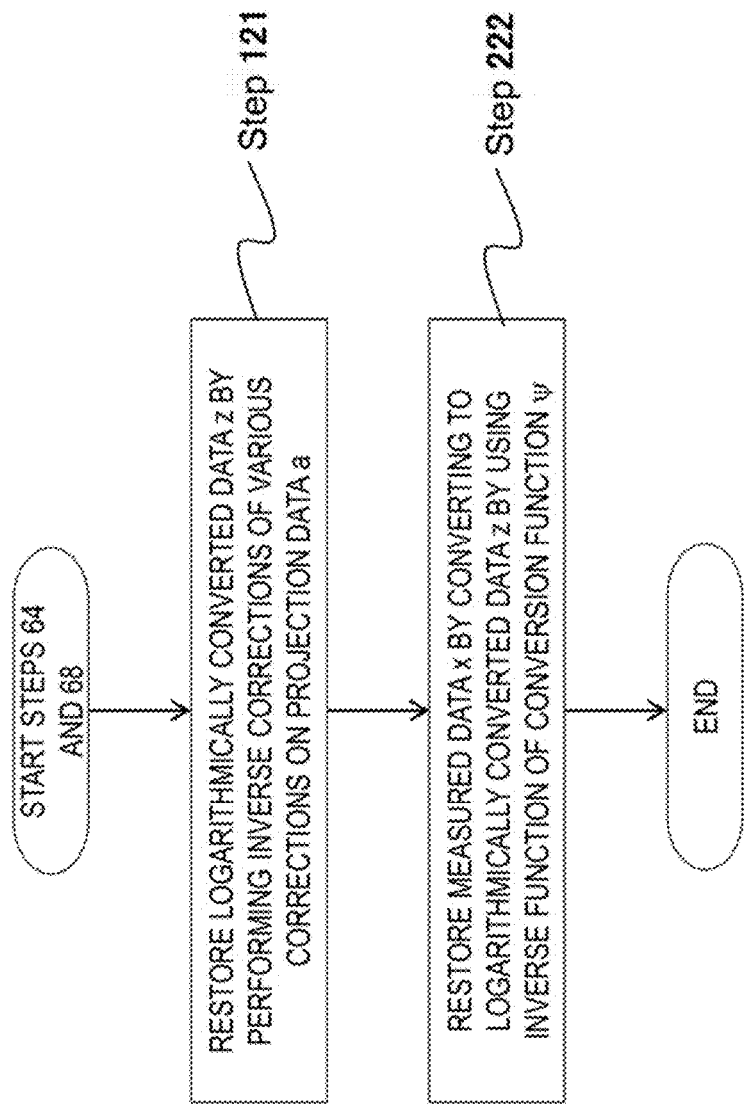
FIG. 13 is a flowchart illustrating an operation of a restorer 24 of the signal processing device 124 of Embodiment 2.

An operation of the signal processing device 124 is illustrated in flowcharts of FIGS. 12 and 13. FIG. 12 illustrates a flow in which an output signal received from the data acquisition system 108 is sequentially converted into the measured data x and the projection data a, the flow showing the same operations as in the flow of FIG. 6 in Embodiment 1. However, the operations in Steps 32 and 33 in the flow of FIG. 6 are performed in a single Step such as Step 232 by the first to third logarithmic converters 215 to 217 of the positive number converter/logarithmic converter 211 in Embodiment 2.

Figure 9:
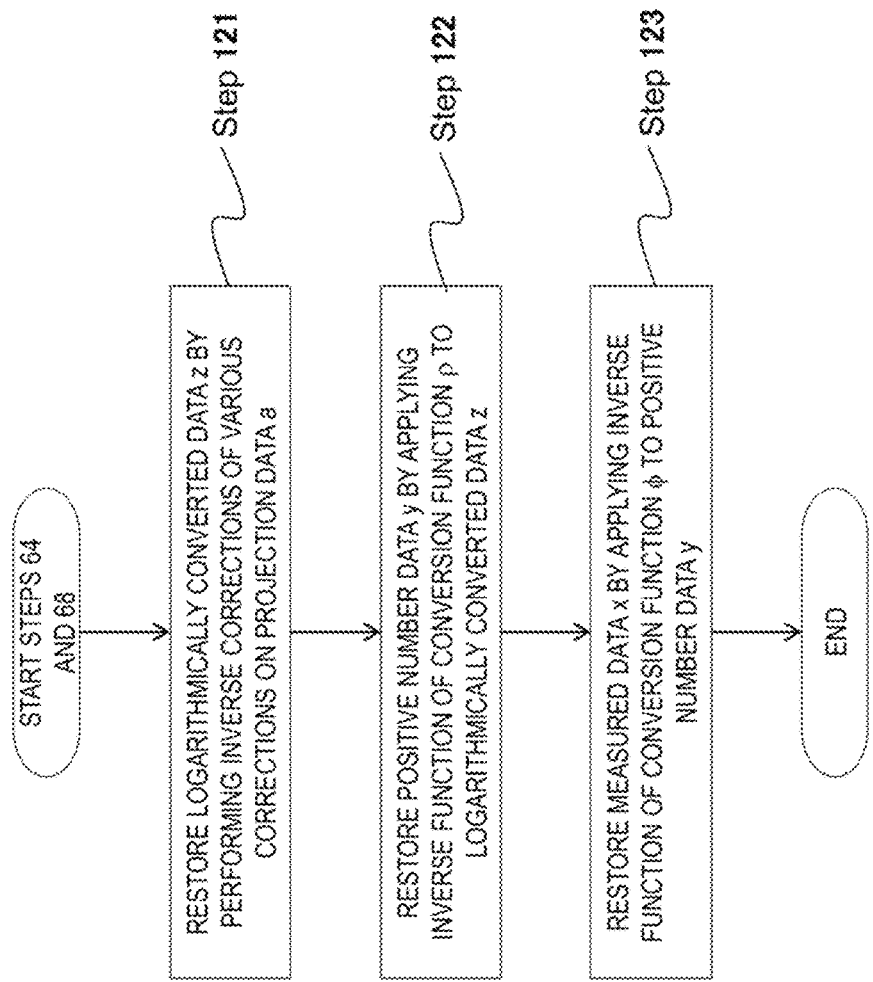
FIG. 9 is a flowchart illustrating an operation of a restorer 24 of the signal processing device 124 of Embodiment 1.

On the other hand, FIG. 13 illustrates a flow in which the measured data x is restored from the projection data a, the flow showing the same operations as in the flow of FIG. 9 in Embodiment 1. However, the operations in Steps 122 and 123 in FIG. 9 are performed in a single Step such as Step 222 by the first and second inverse logarithmic converters 226 and 227 of the restorer in Embodiment 2.

Configurations and operations other than the above-described configurations of the X-ray CT apparatus of Embodiment 2 are the same as those of the X-ray CT apparatus of Embodiment 1, and thus description thereof will be omitted.

<Embodiment 3>

An X-ray CT apparatus of Embodiment 3 will be described. In the X-ray CT apparatus of Embodiment 3, the signal processing device 124 determines whether or not a scanning condition received from the operator via the input device 121 is a predefined low dose scanning condition, and, in a case where a determination result is the low dose scanning condition, the restorer 24 performs restoration of the projection data a stored in the storage device 123 so as to reduce system noise.

Figure 14:
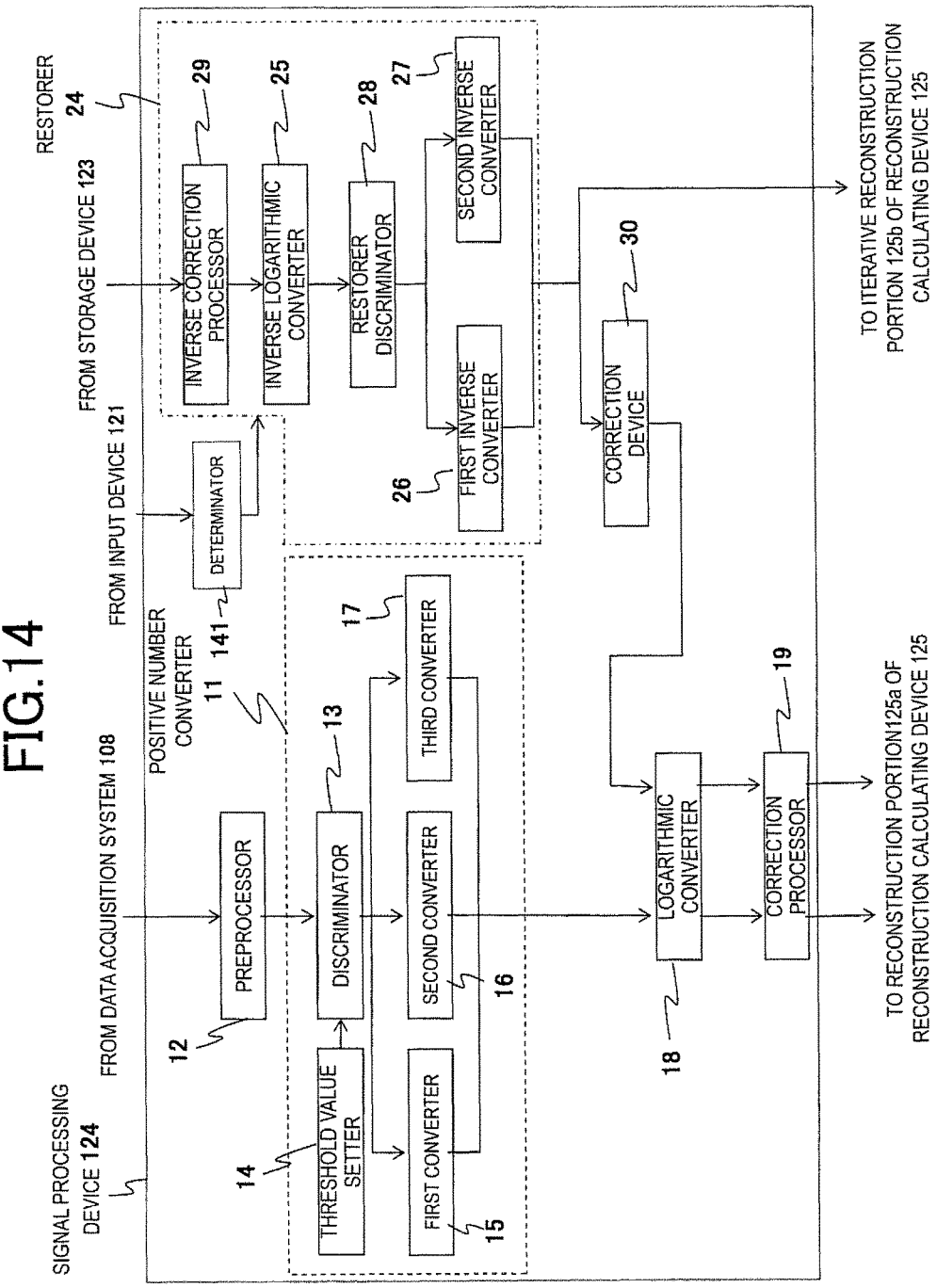
FIG. 14 is a block diagram illustrating a configuration of a signal processing device 124 of Embodiment 3.

In Embodiment 1, an example has been described in which the iterative image reconstruction method or the bias correction is performed depending on a user's selection. In Embodiment 3, in light of the iterative image reconstruction method or the bias correction being necessary in a case of low dose scanning, it is determined whether or not scanning is the low dose scanning, and in the case of low dose scanning, the iterative image reconstruction method or the bias correction is performed. A determinator 141 which performs such determination is provided in the signal processing device 124 as illustrated in FIG. 14.

In a case of a predefined low dose scanning condition, the determinator 141 instructs the restorer 24 to restore the projection data a, so as to reconstruct an image according to the iterative image reconstruction method or the bias correction. Which one of the iterative image reconstruction method or the bias correction is performed may be set in advance, or may be performed by receiving the operator's selection.

For example, in a case where, among conditions in which an irradiation dose is equal to or less than a threshold value, a tube voltage is equal to or less than a threshold value, a rotation speed of the rotation body 115 is equal to or less than a threshold value, an area of a projection value in any view of the projection data a is more than a threshold value, and a signal value of at least one of elements related to the measured data x is equal to or smaller than a threshold value, any one thereof or predetermined two or more combinations are satisfied, the determinator 141 determines a low dose scanning condition. A threshold value for the low dose scanning condition may be input by the operator, or may employ a preset value.

REFERENCE SIGNS LIST

11 POSITIVE NUMBER CONVERTER
12 PREPROCESSOR
13 DISCRIMINATOR
14 THRESHOLD VALUE SETTER
15 FIRST CONVERTER
16 SECOND CONVERTER
17 THIRD CONVERTER
18 LOGARITHMIC CONVERTER
19 CORRECTION PROCESSOR
21, 22, AND 23 ICON
24 RESTORER
25 INVERSE LOGARITHMIC CONVERTER
26 FIRST INVERSE CONVERTER
27 SECOND INVERSE CONVERTER
28 RESTORER DISCRIMINATOR
29 INVERSE CORRECTION PROCESSOR
30 CORRECTION DEVICE
100 SCANNER
109 BED
120 DISPLAY DEVICE
121 INPUT DEVICE
123 STORAGE DEVICE
124 SIGNAL PROCESSING DEVICE
125 RECONSTRUCTION CALCULATING DEVICE
125a RECONSTRUCTION PORTION
125b ITERATIVE RECONSTRUCTION PORTION
131 INPUT/OUTPUT DEVICE
132 IMAGE CALCULATING DEVICE

The invention claimed is:

1. An X-ray CT apparatus comprising:
an X-ray generation device that irradiates an object with X-rays;
a data acquisition system that detects the X-rays passed through the object;
a signal processing device that obtains measured data including signal values of 0 or less by processing an output signal from the data acquisition system, and performs a conversion process on the measured data by using a predefined function including a logarithmic function so as to generate projection data; and
a reconstruction calculating device that performs a reconstruction process on the projection data so as to generate an image,
wherein the predefined function is a function of which an inverse function is present for values of a predetermined negative number or more, and the measured data including signal values of 0 or less within a predetermined range is restored from the projection data by applying the inverse function to the projection data.

2. The X-ray CT apparatus according to claim 1,
wherein the signal processing device includes
a positive number converter that converts the signal values of 0 or less of the measured data into positive number data by using a predefined positive number conversion function; and
a logarithmic converter that performs logarithmic conversion on the positive number data converted by the positive number converter so as to generate the projection data, and wherein the positive number conversion function in the positive number converter is a monotonically increasing function for negative numbers within the predetermined range.

3. The X-ray CT apparatus according to claim 1, further comprising:
a storage device that stores the projection data,
wherein the signal processing device includes a restorer that reads the projection data stored in the storage device, and that restores the measured data including the signal values of 0 or less within the predetermined range.

4. The X-ray CT apparatus according to claim 3,
wherein the signal processing device includes a correction device that performs correction on the measured data restored by the restorer.

5. The X-ray CT apparatus according to claim 3,
wherein the reconstruction calculating device includes an iterative reconstruction portion that performs iterative image reconstruction on the measured data restored by the restorer, so as to generate an image.

6. The X-ray CT apparatus according to claim 3, further comprising:
an input device that receives a selection of normal image reconstruction or image reconstruction using the measured data restored by the restorer from an operator,
wherein the signal processing device performs restoration on the projection data stored in the storage device by using the restorer in a case where the selection received by the input device is the image reconstruction using the measured data restored by the restorer.

7. The X-ray CT apparatus according to claim 3, further comprising:
an input device that receives setting of a scanning condition from an operator,
wherein the signal processing device determines whether or not the scanning condition received by the input device is a predefined low dose scanning condition, and performs restoration on the projection data stored in the storage device by using the restorer in a case where a determination result is the low dose scanning condition.

8. An image calculating device for an X-ray CT apparatus, comprising:
a signal processing device that obtains measured data, including signal values of 0 or less by processing a signal obtained by detecting X-rays passed through an object, and performs a logarithmic conversion on the measured data by using a predefined function so as to generate projection data; and
a reconstruction calculating device that performs a reconstruction process on the projection data so as to generate an image,
wherein the predefined function is a function of which an inverse function is present for values of a predetermined negative number or more, and the measured data including signal values of 0 or less within a predetermined range is restored by applying the inverse function to the projection data.

9. An X-ray CT apparatus comprising:
an X-ray generation device that irradiates an object with X-rays;
a data acquisition system that detects the X-rays passed through the object;
a signal processing device that obtains measured data including signal values of 0 or less by processing an output, signal from the data acquisition system, and performs a conversion process on the measured data by using a predefined function including a logarithmic function so as to generate projection data;
a reconstruction calculating device that performs a reconstruction process on the projection data so as to generate an image; and
a storage device that stores the projection data,
wherein the signal processing device includes a restorer that reads the projection data stored in the storage device, and that restores the measured data including the signal values of 0 or less within a predetermined range.

* * * * *